(12) United States Patent
Mayes

(10) Patent No.: US 6,939,514 B1
(45) Date of Patent: Sep. 6, 2005

(54) METHOD AND APPARATUS FOR DISPENSING AND DISTRIBUTING BIOLOGICAL SAMPLE

(75) Inventor: Ronald A. Mayes, Beaumont, TX (US)

(73) Assignee: Helena Laboratories Corporation, Beaumont, TX (US)

( * ) Notice: Subject to any disclaimer, the term of this patent is extended or adjusted under 35 U.S.C. 154(b) by 1511 days.

(21) Appl. No.: 08/747,046

(22) Filed: Nov. 12, 1996

Related U.S. Application Data

(63) Continuation-in-part of application No. 08/548,452, filed on Oct. 26, 1995, now Pat. No. 5,697,522, which is a continuation of application No. 08/313,400, filed on Sep. 27, 1994, now abandoned, which is a continuation of application No. 08/060,977, filed on May 14, 1993, now abandoned.

(60) Provisional application No. 60/016,942, filed on May 6, 1996.

(51) Int. Cl.⁷ .............................................. B01L 3/02
(52) U.S. Cl. .................................................... 422/100
(58) Field of Search ........................ 422/100; 401/139

(56) References Cited

U.S. PATENT DOCUMENTS

| | | | |
|---|---|---|---|
| 2,982,987 A | * | 5/1961 | Knapp ........................ 401/139 |
| 3,366,278 A | | 1/1968 | Forbes |
| 3,788,528 A | | 1/1974 | Ogle |
| 4,411,661 A | | 10/1983 | Kersten |
| 4,563,104 A | * | 1/1986 | Saint-Amand .............. 401/139 |
| 4,811,866 A | | 3/1989 | Golias |
| 4,925,065 A | | 5/1990 | Golias |
| 5,024,355 A | | 6/1991 | Jouillat et al. |
| 5,086,950 A | | 2/1992 | Crossdale et al. |
| 5,114,033 A | | 5/1992 | Golias et al. |
| 5,139,174 A | | 8/1992 | Golias |
| 5,163,583 A | | 11/1992 | Whitworth |
| 5,286,453 A | | 2/1994 | Pope |
| 5,801,062 A | * | 9/1998 | Sarstedt et al. ............. 436/180 |

* cited by examiner

*Primary Examiner*—Jeffrey R. Snay
(74) *Attorney, Agent, or Firm*—DLA Piper Rudnick Gray Cary US LLP

(57) ABSTRACT

The invention is a method and apparatus to dispense and spread a liquid from a storage container onto a surface. An inventive paddle is attached to an apparatus which is inserted into a storage container, such as a test tube. After dispensing the sample, the storage container is manipulated such that the paddle smears, crushes, or distributes the dispensed sample. Therefore, it is unnecessary to set aside the storage container to perform a smear procedure on a dispensed sample of blood. This increases the safety, speed, and efficiency of the smear procedure, and reduces the risk that the sample will be contaminated. The invention further discloses a method and apparatus for using temperature differential, rather than mechanical force, to safely dispense hazardous biological and chemical samples from a storage container such as a test tube.

14 Claims, 10 Drawing Sheets

Fig 2
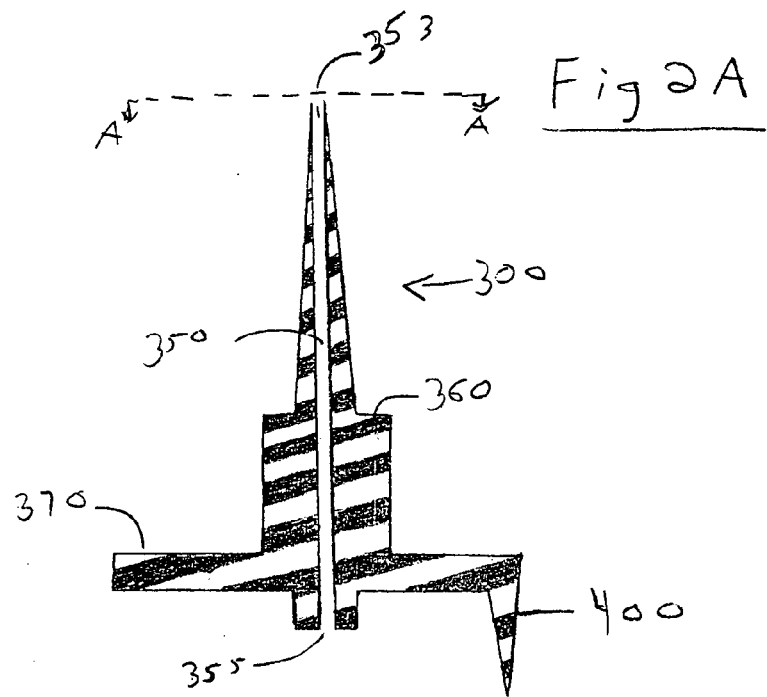
Fig 2A
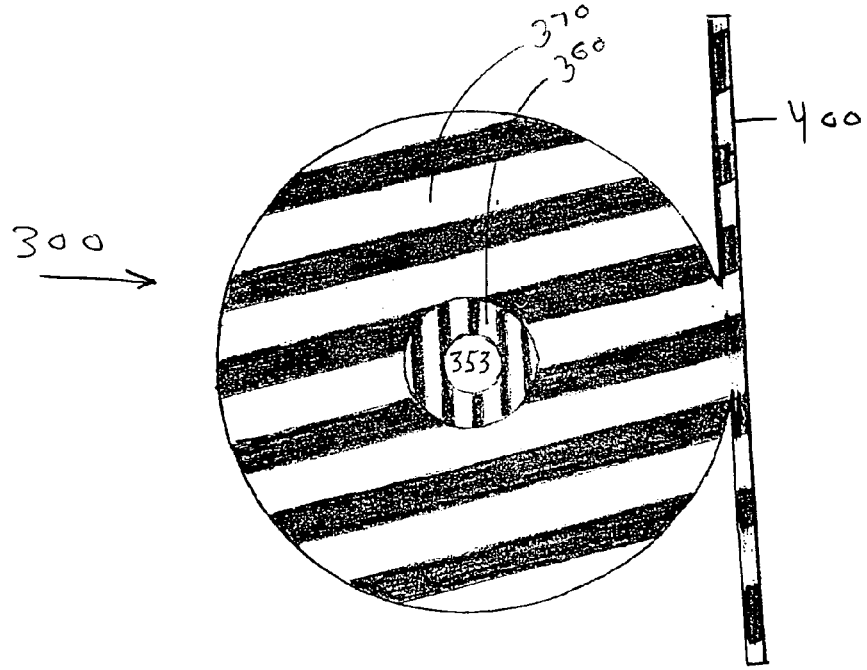
Fig 2B

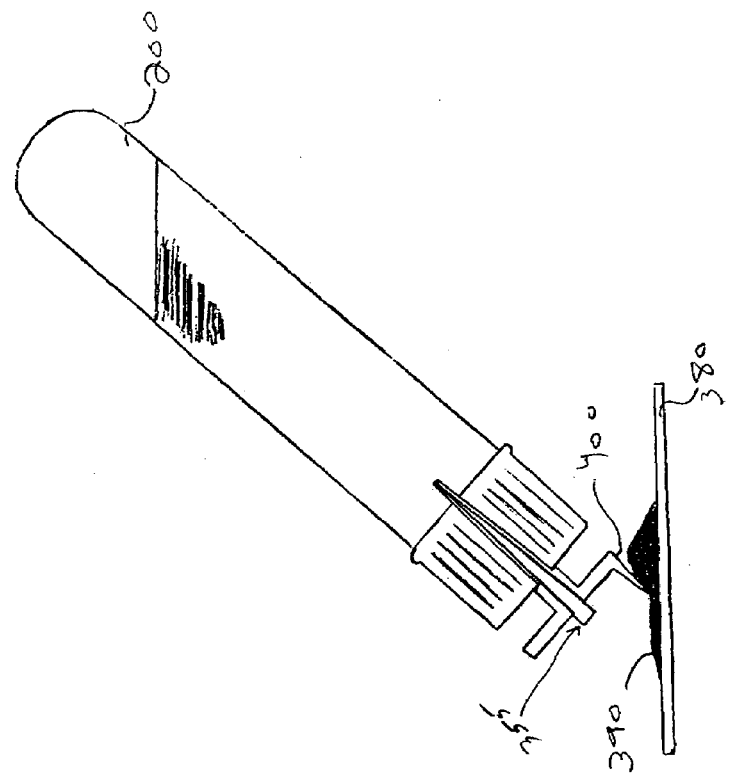
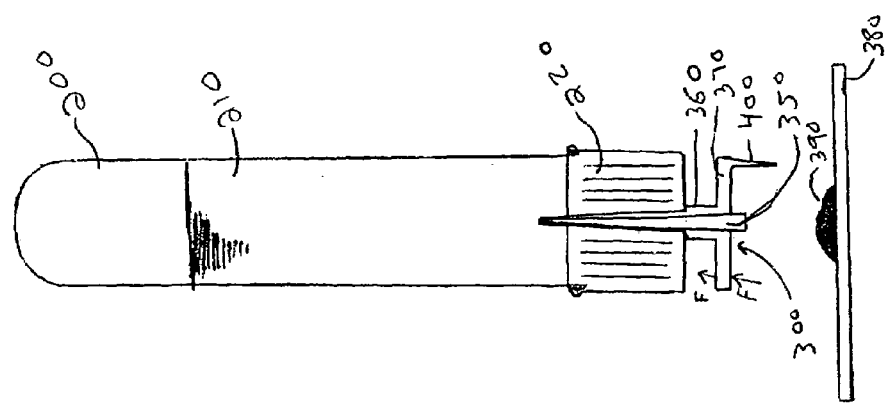

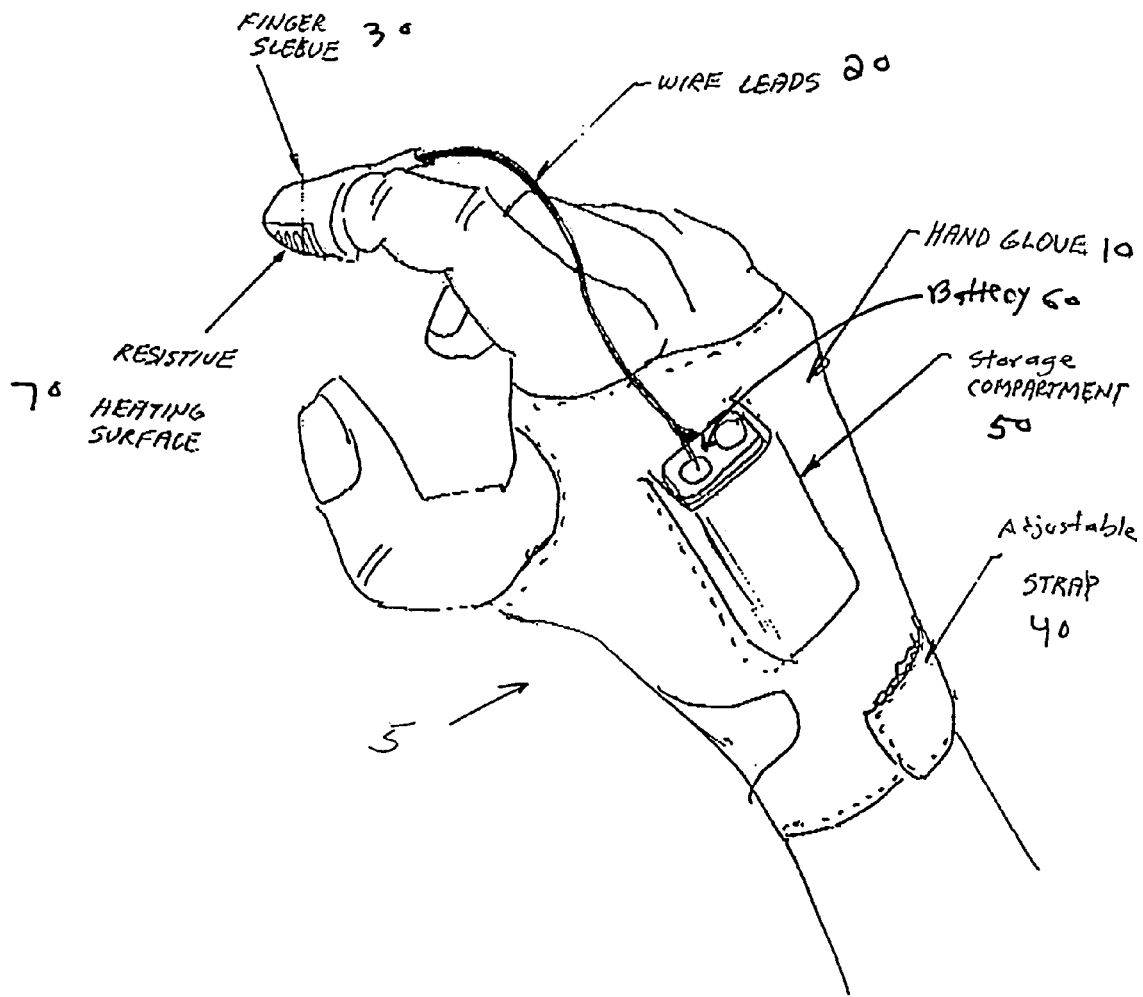

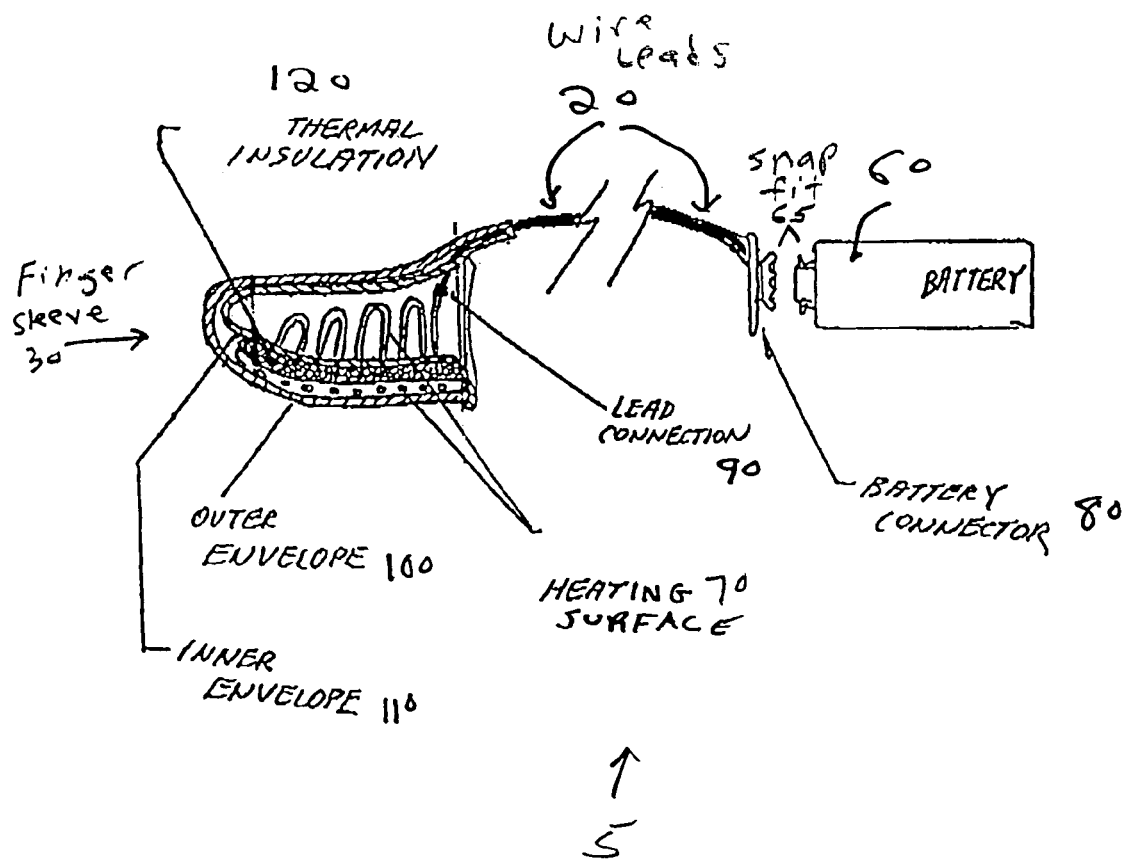

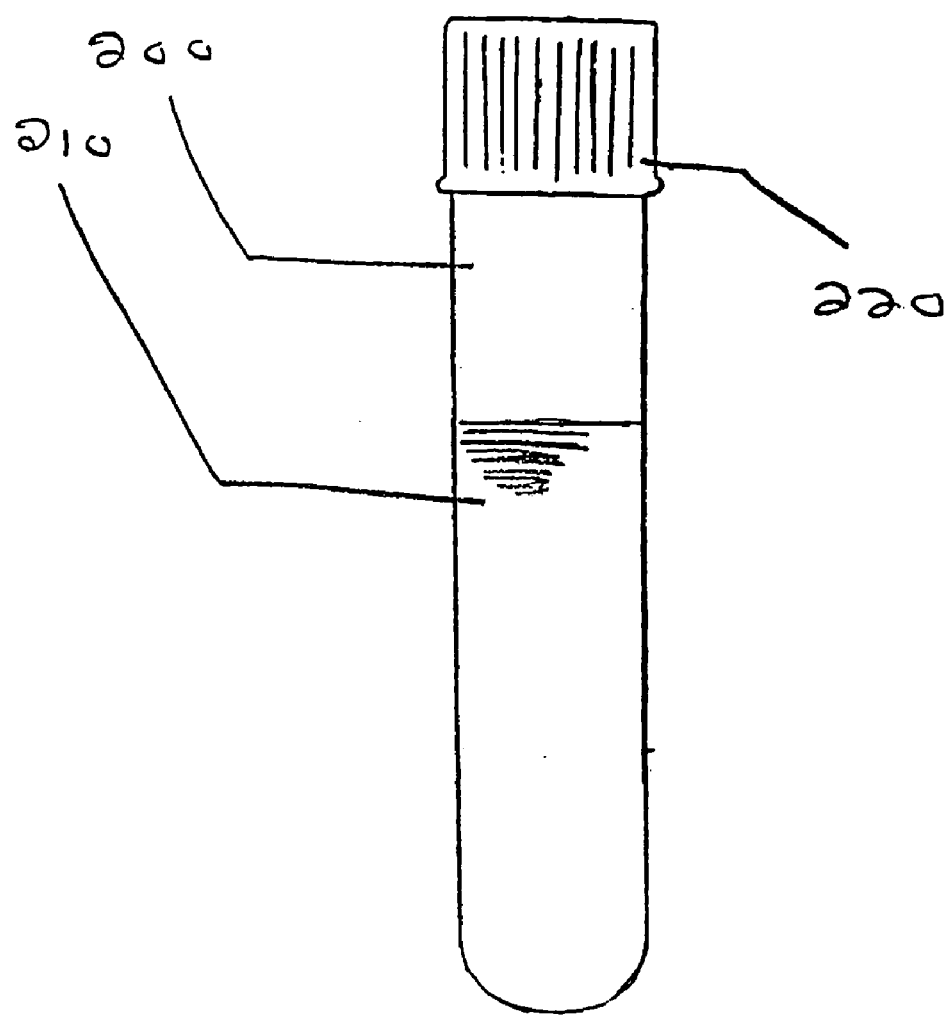

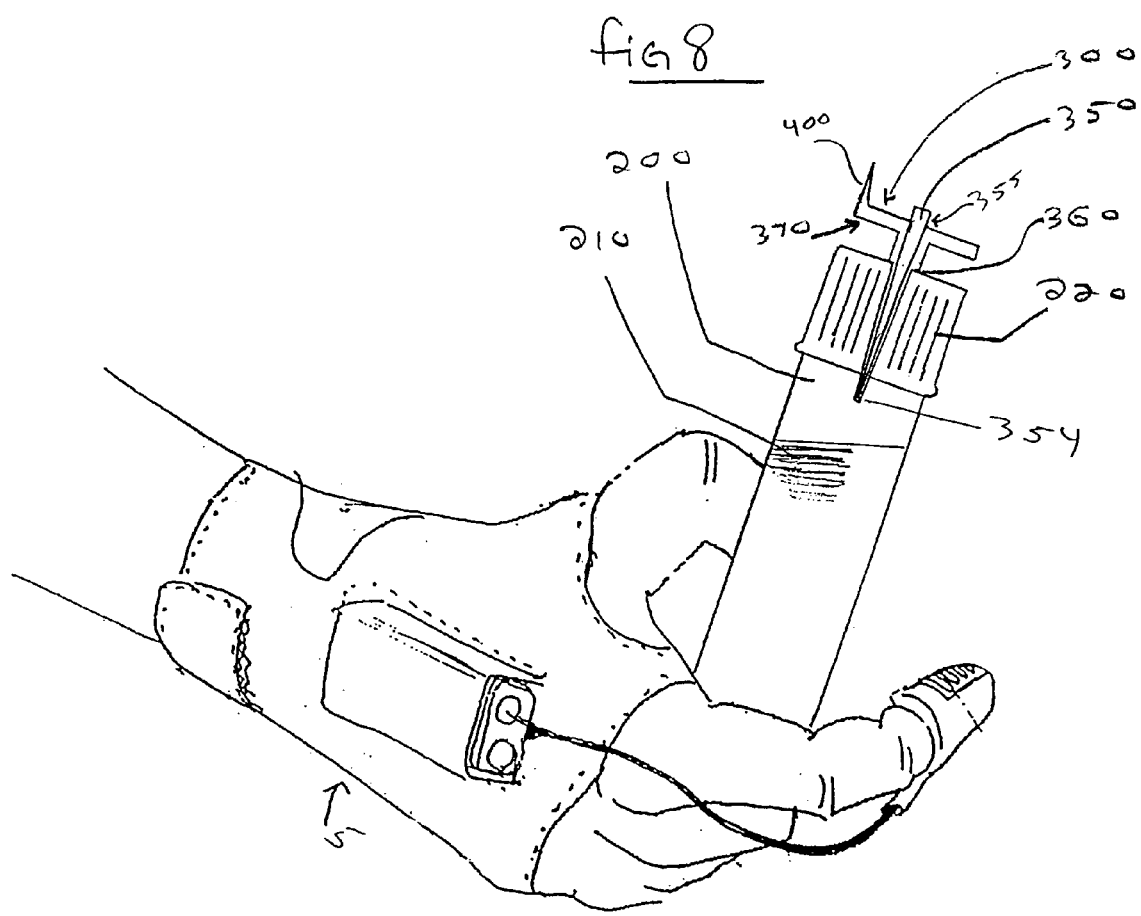

METHOD AND APPARATUS FOR DISPENSING AND DISTRIBUTING BIOLOGICAL SAMPLE

CROSS-REFERENCE TO RELATED APPLICATIONS

This application is a continuation-in-part of provisional application Ser. No. 60/016,942, entitled "Method and Apparatus for Heating Biological Sample", by Ronald A. Mayes, filed on May 6, 1996; and a continuation-in-part of application Ser. No. 08/548,452, entitled "Test Tube Drop Dispenser", filed on Oct. 26, 1995 now U.S. Pat. No. 5,697,522 by Ronald A. Mayes (itself a continuation of Ser. No. 08/313,400 filed on Sep. 27, 1994, now abandoned, which is a continuation of Ser. No. 08/060,977, filed May 14, 1993, now abandoned). Each of the foregoing is incorporated by reference.

The present invention relates to copending application Ser. No. 08/747,045, to Tipton L. Golias and Ronald A. Mayes, filed on even date herewith, and entitled METHOD AND APPARATUS FOR HEATING AND DISPENSING BIOLOGICAL SAMPLE, the disclosure of which is incorporated herein by reference.

BACKGROUND OF THE INVENTION

The invention of this application relates to dispensing a liquid sample and distributing the sample on a surface.

1. Field of the Invention

The present invention has particular application to the medical and laboratory diagnostic fields. In these fields, it is often necessary to dispense liquids from conventional containers, such as test tubes, onto a surface, and then distribute the dispensed liquid on the surface. Because the distributing operation can be dangerous if performed with substances that are hazardous, toxic, or infectious, the invention is further related to the field of laboratory and worker safety.

2. Description of the Related Art

The invention is generally related to the following United States patents dealing with dispensing liquids from a container, the disclosures of which are hereby incorporated by reference: U.S. Pat. No. 4,811,866, Golias, issued Mar. 14, 1989; U.S. Pat. No. 4,925,065, Golias, issued May 15, 1990; U.S. Pat. No. 5,114,033, Golias et al, issued May 19, 1992; and U.S. Pat. No. 5,139,174, Golias, issued Aug. 18, 1992.

Other patents in the prior art include the following: U.S. Pat. No. 3,366,278, to Fobes, issued on Jan. 30, 1968; U.S. Pat. No. 3,788,528, to Ogle, issued on Jan. 29, 1974; U.S. Pat. No. 4,411,661, to Kersten, issued on Oct. 25, 1983; U.S. Pat. No. 5,024,355, to Jouillat et al, issued on Jun. 18, 1991; U.S. Pat. No. 5,086,950, to Crossdale et al, issued on Feb. 11, 1992; U.S. Pat. No. 5,163,583, to Whitworth, issued on Nov. 17, 1992; and U.S. Pat. No. 5,286,453, to Pope, issued on Feb. 15, 1994.

A task often performed in the chemical and biological field is the dispensing of liquid samples from sealed or unsealed containers, such as test tubes and vacuum tubes. As disclosed in U.S. Pat. No. 5,286,453, issued Feb. 15, 1994 to Pope, it is often necessary to isolate the liquid sample from the laboratory technician for safety reasons, such as where the sample is a hazardous, toxic, or infectious substance. Another reason to isolate the sample from the technician is to prevent contamination of the sample.

As further disclosed in the '453 patent, certain tests require the technician to spread a liquid sample on a glass slide. For example, a proper spread or blood distribution is an important hematologic procedure that is required to perform many hematologic diagnoses.

Smearing may be accomplished by a number of prior art techniques, many of which involve a technician's handling of the glass slide containing the sample. One technique of the prior art is for a laboratory technician to wipe a "clean" glass slide together with the slide containing the sample which "smears" the sample on each. This smearing technique can jeopardize both the health of the lab technician and the purity of the sample being smeared. Where the sample is a hazardous substance, the technician must take great care to properly rub the two glass slides together. The slides must not puncture the technician's skin or any protective gloves or coverings which the technician is wearing. Further, the sample must not rub off onto the technician, where it could be contacted or transmitted in the future.

Undesirable contamination of the sample is a problematic characteristic of this prior art technique because it is difficult to isolate each "clean" glass slide from foreign substances.

Another disadvantage of this prior art smearing technique is that it is inefficient and time consuming. The technician is unable to quickly dispense and smear samples because both hands must be used in the smearing step. Thus, the dispensing container must be placed aside by the technician while the smearing step is performed. Therefore, it is difficult to rapidly dispense and smear many samples consecutively.

The '453 patent, previously discussed, discloses a device for dispensing liquid, such as blood, onto a glass slide. The dispensing device disclosed in the '453 patent is undesirable because, while it attempts to address the step of dispensing hazardous blood onto a glass slide, it does not address the step of smearing the hazardous blood onto the slide. The techniques of the prior art must be used with the device of the '453 patent to smear the dispensed blood on the slide, consequently resulting in the problems previously described concerning technician safety, sample contamination, and inefficiency.

What is needed is a method of dispensing and distributing hazardous samples onto a surface, without exposing the technician to the hazardous sample.

What is needed is a method of dispensing and distributing samples onto a surface without contaminating the samples.

What is needed is a efficient method of dispensing and smearing samples onto a surface so that numerous dispense-smear steps can be performed in sequence.

SUMMARY AND OBJECTS OF THE INVENTION

The present invention provides a unique dispenser apparatus designed to allow laboratory technicians to easily dispense and spread samples onto a surface. The dispenser contains a cannula for allowing dispersal of a substance from a container, and also contains an integral paddle that is used to spread the sample immediately following the dispensing of the sample. Using the present invention, a technician may dispense and smear a hazardous blood sample onto a glass slide with a single hand.

It is an object of the invention to provide an apparatus for dispensing and distributing samples onto a surface, without exposing the technician to the sample.

It is an object of the invention to provide an apparatus for distributing samples onto a surface without contaminating the samples.

It is an object of the invention to provide an apparatus for dispensing and distributing samples onto a surface so that numerous dispense-spread steps can be performed in rapid sequence.

BRIEF DESCRIPTION OF THE DRAWINGS

The foregoing objects and advantages of the present invention, together with other advantages which may be attained by its use, will become more apparent upon reading the following detailed description of the invention in conjunction with the drawings. In the drawings, wherein like reference numerals identify corresponding components:

FIG. 2A shows a cross-sectional view of the dispensing apparatus of the present invention;

FIG. 2B shows an underside view along lines A—A of FIG. 2A of the dispensing apparatus of the present invention;

FIG. 3 shows a cross-sectional view of the dispensing apparatus of the present invention inserted into a vacuum tube where a sample has been dispensed;

FIG. 4 shows a cross-sectional view of the dispensing apparatus of the present invention where the paddle of the dispensing apparatus is used to spread the sample of FIG. 3.

FIG. 5 is a diagrammatic illustration of a heating apparatus of an embodiment of the present invention;

FIG. 6 is a diagrammatic, partially cross-sectional illustration of the construction of the embodiment of the invention shown in FIG. 5;

FIGS. 7, 8, 9 and 10 show cross-sectional illustrations of a method of the present invention whereby the heating apparatus of FIGS. 5 and 6 is used to safely dispense a hazardous substance from a storage container.

DETAILED DESCRIPTION OF THE INVENTION

The present invention provides a dispensing apparatus that may be used with storage devices of the prior art, such as a container or test tube. As used herein the term "distributing" is intended to encompass all devices and mechanisms of any kind which can be used to apply a sample, of any form, onto a substrate. The term "distributing" is further intended to encompass all methods of any kind including, by way of example and not by way of limitation, spreading, crushing, smearing, and regardless of any discontinuity and/or lack of homogeneity or uniformity in the result.

Figure 1:
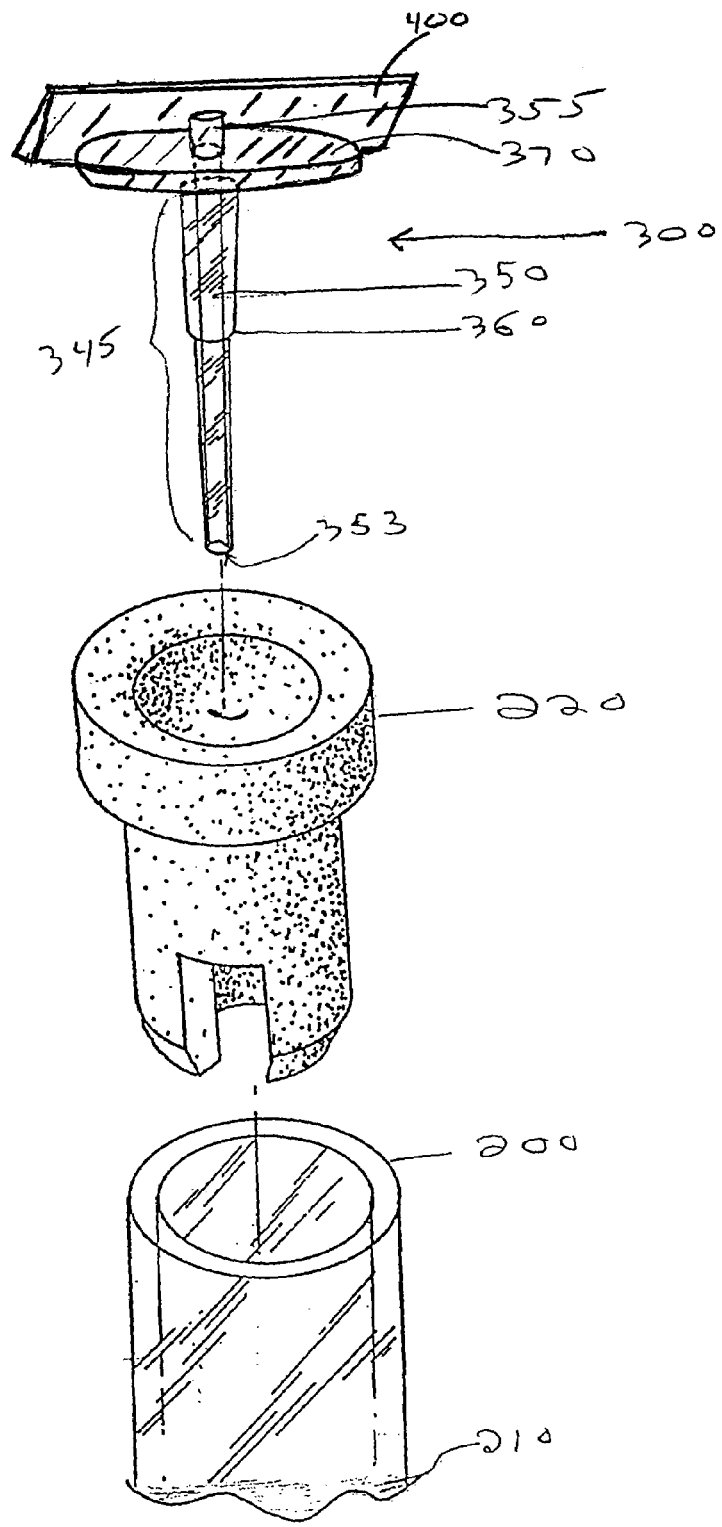
FIG. 1 shows a three dimensional view of the dispensing apparatus of the present invention and how it is inserted into a test tube.

FIG. 1 shows the dispensing apparatus of the present invention generally at 300. The dispensing apparatus is inserted through a conventional rubber test tube stopper 220, either prior to insertion of the stopper 220 into test tube 200, or after the stopper has been inserted into test tube 200. The test tube 200 contains a liquid 210. The liquid 210 may be a biological or chemical substance, and may be hazardous, toxic, or infectious.

With continued reference to FIG. 1, the dispensing apparatus 300 is formed as a cannula, containing channel 350 and a lip or shoulder 360. The channel 350 has an entrance portion 353 and an exit portion 355. The shoulder 360 is preferably perpendicular to the channel 350. A ledge 370 is used by a technician to insert the dispensing apparatus 300 into the stopper 220 or other storage lid. The exit portion 355 of the channel 350 preferably extends past the ledge 370.

The exterior of the cannula entrance 353 is preferably constructed as a pointed tip which is sufficiently sharp to pierce a typical rubber stopper or lid. The tip 353 functions to break a seal on a sealed container to allow pressure to equalize between the inside of the container and the outside of the container. Alternatively, an unsealed container with a preformed or predrilled hole or opening in the stopper or covering may be used. In such a case, the pressure is already equalized and the dispensing apparatus 300 is positioned by sliding it through the preformed hole or opening.

As used herein, the term "pierce" is intended to cover all methods of inserting the dispensing apparatus 300, including the case where the tip 353 penetrates through the rubber on the rubber stopper 220 and the case where the stopper has a preformed hole which allows the dispensing apparatus to be easily slid through the rubber stopper 220. In each case the result is that the dispensing apparatus 300 "pierces" the stopper 220.

The ledge 360 is optional when the apparatus 300 is heated to dispense a sample, as discussed below with reference to FIG. 8.

A paddle 400 is incorporated into the dispensing apparatus 300 for use in distributing the sample after it has been dispensed. The paddle 400 is preferably perpendicular to the ledge 370 and parallel to the channel 350. The paddle 400 preferably extends past the cannula exit 355.

The channel 350, shoulder 360, ledge 370, and paddle 400 may be formed integrally with each other (as shown) or may be attached separately. Attachment may be by any suitable method such as by glue, cement or snap-fitting. The apparatus is preferably constructed of molded plastic. Alternatively, the apparatus is a single piece of glass or pyrex, formed by known techniques.

Although the exterior 345 of the channel 350 is shown tapered from the ledge 370 to the entrance 353, tapering is not required. The only requirement is that the apparatus 300 be able to fit through or pierce stopper 220, or otherwise pass through a surface of the container from which a sample is desired.

While the channel 350 is not shown tapered, the channel could be tapered. If tapered, the channel 350 is preferably tapered from ledge 370 towards entrance 353 (FIGS. 3–4).

FIG. 2A shows a cross-sectional view of the dispenser 300 of the present invention. The paddle 400, ledge 370, shoulder 360 and channel 350 are shown. As with FIG. 1, the entrance opening 353 is pointed on the exterior, and the exit opening 355 extends a short distance away from ledge 370.

FIG. 2B shows a bottom view of the inventive dispensing apparatus along lines A—A of FIG. 2A. As shown, the channel 350 preferably has a round entrance 353 at the end of the insert portion of apparatus 300. Alternatively, the cannula entrance 353 is offset or tapered from the end of the channel 350. FIG. 2B also shows the paddle 400 aligned tangentially to the round ledge 370, although any position which allows distributing of the sample is suitable.

The preferred shape of the paddle 400, as shown in FIGS. 1, 2A and 2B, is a rectangular longitudinal projection which tapers to a point or tip. The paddle 400 shown resembles a squeegee in cross-sectional shape. Alternatively, the paddle 400 may be any suitable shape useful for distributing or crushing a dispensed sample, such as square or round. Likewise, the paddle may taper into any suitable edge. If the paddle is used to crush a sample, it may have no edge (i.e. a "flat" edge).

FIG. 3 shows one method of how samples are dispensed using the apparatus 300 of the present invention. FIG. 3 shows a test tube 200 containing a sample liquid 210. The test tube 200 is sealed via a flexible rubber stopper 220.

Although a test tube 200 is preferred, any container having a lid or cover which is able to hold apparatus 300 may be used with the present invention, including a vacuum tube. The rubber stopper 220 may be inserted in and around the container 200, as shown, or may be inserted only in the container opening. The liquid 210 may be a hazardous, toxic, or infectious substance, or any other liquid.

In using the present invention, the apparatus 300 is inserted into the lid of the container, such as the test tube 200, as previously shown and described with respect to FIG. 1. The tube 200 is then inverted to the position shown in FIG. 3 and held over a surface, such as a glass slide 380, on which it is desired to dispense a sample.

Next, a force F is applied to the ledge 370, causing the shoulder 360 to compress the rubber stopper 220. The compression of the rubber stopper 220 causes the pressure inside the test tube 200 to increase. This increase of pressure forces liquid 210 out of the test tube 200 through channel 350, to form a deposit of liquid 390 on the glass slide 380.

Rather than apply a force F directly to the ledge 370, the force could be applied to the paddle 400. This may be performed either by pushing the paddle upwards, or by pushing the test tube downwards so that the paddle is forced against the surface of the glass slide 380. A force applied to the paddle 400 is transferred to the ledge 370 which holds the paddle 400 away from the channel 350 and exit opening 355.

With reference to FIG. 4, the dispensing apparatus 400 is next used to spread the sample 390. This operation is performed simply by tipping the test tube 200 on its edge and scraping the paddle 400 over the sample 390, as shown. As shown in the Figure and previously described, the paddle 400 preferably extends beyond the cannula exit opening 355. This increases the ease of performing the distributing operation. While FIG. 4 shows distributing occurring at an acute angle, a paddle 400 which extends far beyond cannula exit opening 355 is be able to spread the sample 390 at an obtuse angle, approaching 180 degrees.

If the sample is a substance which solidifies on contact with air, the paddle 400 may have a square edge or circular edge to mash or compress the sample 390.

By tipping the container and applying a force on the container to scrape the sample 390 with the paddle 400 on the dispensing apparatus 300, it is unnecessary to set aside the container 200 in order to find a "clean" glass slide to rub with the sample slide 380. The process of distributing and smearing is therefore greatly simplified.

Because it is unnecessary to rub two sharp glass slides together, the safety of the "smearing" step is increased. The technician may hold the test tube 200 at the end opposite the paddle and still control the paddle and how the sample 390 is spread or smeared. By holding the end of the test tube 200, the technician's hands are kept far away from any hazardous or toxic sample which may be dispensed on the slide 380.

The same apparatus 300 and paddle 400 may be used for multiple samples. This decreases the risk of contamination of samples, since it is unnecessary to introduce a number of foreign slides to rub with the slide 380 on which the sample is dispensed.

Therefore, it is evident that the present invention increases the safety of dispensing samples of hazardous liquids from containers. It also increases the speed and efficiency at which samples can be provided and spread, and at the same time reduces the risk of contamination of the sample.

The prior examples utilize a method of depositing a sample from test tube 200 which involves the application of force to the dispensing apparatus 300. Specifically, force is applied to ledge 370. Where the liquid 210 is a hazardous substance, it is advantageous to use a method not employing the application of physical force to the dispensing apparatus 300.

Accordingly, a preferred embodiment of the present invention utilizes heat to dispense the sample 390 from the container. Such a method is disclosed in previously mentioned copending application Ser. No. 08/747,045, to Ronald A. Mayes and Tipton L. Golias, filed on even date herewith, and entitled METHOD AND APPARATUS FOR HEATING AND DISPENSING BIOLOGICAL SAMPLE, the disclosure of which is incorporated herein by reference.

FIGS. 5, 6, 7, 8, 9, 10 and 11 show an apparatus and method using heat rather than physical force to dispose a sample from a test tube.

With reference to FIG. 5, the heating apparatus 5 of the present invention includes a hand glove 10, wire leads 20 and finger sleeve 30. The wire leads 20 are preferably flexible and insulated.

The hand glove 10 covers the palm and back of the hand, but in the illustrated embodiment does not cover the thumb or fingers. Since it is desired that the glove may be worn by persons of different hand sizes, the glove 10 includes an adjustable strap 40 such that it may be snugly secured over the hand of the person wearing the glove. The strap may be of the hook and loop (Velcro®) type or any other conventional design. The glove 10 also contains a storage compartment 50 to hold an energy source. Typically, the energy source will be a battery 60, although any other conventional type of energy source may be employed.

The finger sleeve 30 contains a resistive heating surface 70. The surface 70 is designed to generate heat in response to the receipt of energy from the battery 60. Preferably, the resistive heating surface 70 is constructed of Kapton, or a similar material which provides suitable heat in response to a low (9 volt) voltage from the battery 60.

FIG. 6 shows a diagrammatic partially cross-sectional illustration of the heating apparatus 5. As shown, the battery 60 is connected through a snap-fit connector 65 to wire leads 20. The wire leads 20 connect through lead connection 90 to heating surface 70 at the finger sleeve 30. In the finger sleeve 30, an outer envelope 100 and inner envelope 110 surround the heating surface 70. Thermal insulation 120 is placed between the inner envelope 110 and the heating surface 70.

As shown in FIG. 6, the conventional terminals from battery 60 are snap-fit via connection 65 to a battery connector 80. The battery connector 80 is coupled via the wire leads 20 through a typical lead connection 90 to the finger sleeve 30. The lead connection 90 may be permanent, as by crimping or soldering, or may be removable, as with a mating plug.

As shown in greater detail in FIG. 6, the finger sleeve 30, which is hollow and closed at one end, contains a heating surface 70. Preferably, the heating surface 70 is a combination of resistive metal heating elements which are enclosed by Kapton or rubber. The heating surface is surrounded on the outer side by an outer envelope 100. This envelope is preferably latex. An inner envelope 110 is positioned along the interior of the heating surface 70 so as to be in contact with the finger of the laboratory technician. This inner envelope 100 is preferably constructed with latex. A thermal insulation layer 120 is disposed between the heating surface 70 and the inner envelope 110 to prevent excessive heat from reaching the finger of the laboratory technician. The thermal insulation 120 is preferably foam or other conventional insulation.

In use, current is drawn from battery 60 through battery connector 80 and along wire leads 20. The heating surface 70 increases in temperature when the current flows through the resistive metal elements. The heat from surface 70 radiates through the outer envelope 100. The user may heat samples by merely touching the outer envelope 100 to the sample or container holding the sample, or may place the outer envelope 100 close to the sample or container. The finger of the laboratory technician is insulated from any heat generated by the heating element, by thermal insulation 120. Therefore, the laboratory technician will not be injured if the invention is utilized properly for extended durations of time.

Of course, the glove and sleeve of the present invention are preferably made from nonflammable material to increase safety. For example, hand glove 10 should not burn or harm the user if it is contacted by heating surface 70. Although the glove 10 as illustrated does not cover the fingers of the laboratory technician, a full glove which covers one or more fingers may be desirable, especially if the temperature of the heating surface will be significantly elevated.

The heating surface 70 is preferably contoured such that it conforms to surfaces which are perpendicular or parallel to the finger of the laboratory technician. Thus, minimal effort is needed to make contact between the heating surface 70 of the finger sleeve 30 and a test tube 200 or other container.

As discussed previously, the dispensing of hazardous substances from containers, such as test tubes, must be carefully performed to ensure the safety of the technician performing the dispensing procedure.

FIGS. 7, 8, 9 and 10 show examples of how the present invention is utilized to dispense liquid samples from a container and spread the sample. First, with reference to FIG. 7, a test tube 200 holds a hazardous (or other) liquid 210. The liquid may be blood that is suspected to contain a disease or infection, such as the HIV virus. It is desired to remove a sample of this liquid (blood) 210 from the test tube 200. A rubber stopper 220 seals the test tube to prevent accidental spillage and to prevent contamination of the liquid 210.

As shown in FIG. 8, a technician wearing the heating apparatus 5 of the present invention grasps the test tube 200. As is also shown, the dispensing apparatus 300 described herein is placed through the rubber stopper 220. The apparatus 300 may be pierced through the rubber stopper either prior to, or after, the technician grasps the test tube in the position shown in FIG. 8.

In this embodiment, the shoulder 360 is not required and is considered optional. In the present description, the shoulder 360 is shown as a preferred embodiment of the invention, and is helpful when the dispensing apparatus 300 is manually inserted into stopper 220. However, a technician or machine could successfully insert the dispensing apparatus 300 properly without the stopping feature offered by the shoulder 360.

In this embodiment, the ledge 370 need not extend completely around the exit opening 355. The only requirement for the dispensing apparatus 300 is that a channel 350 connect the interior of the container to the exterior and that the ledge 370 hold the paddle 400 in a position where it can be used to spread the sample by manipulation of the container 200.

Figure 9:
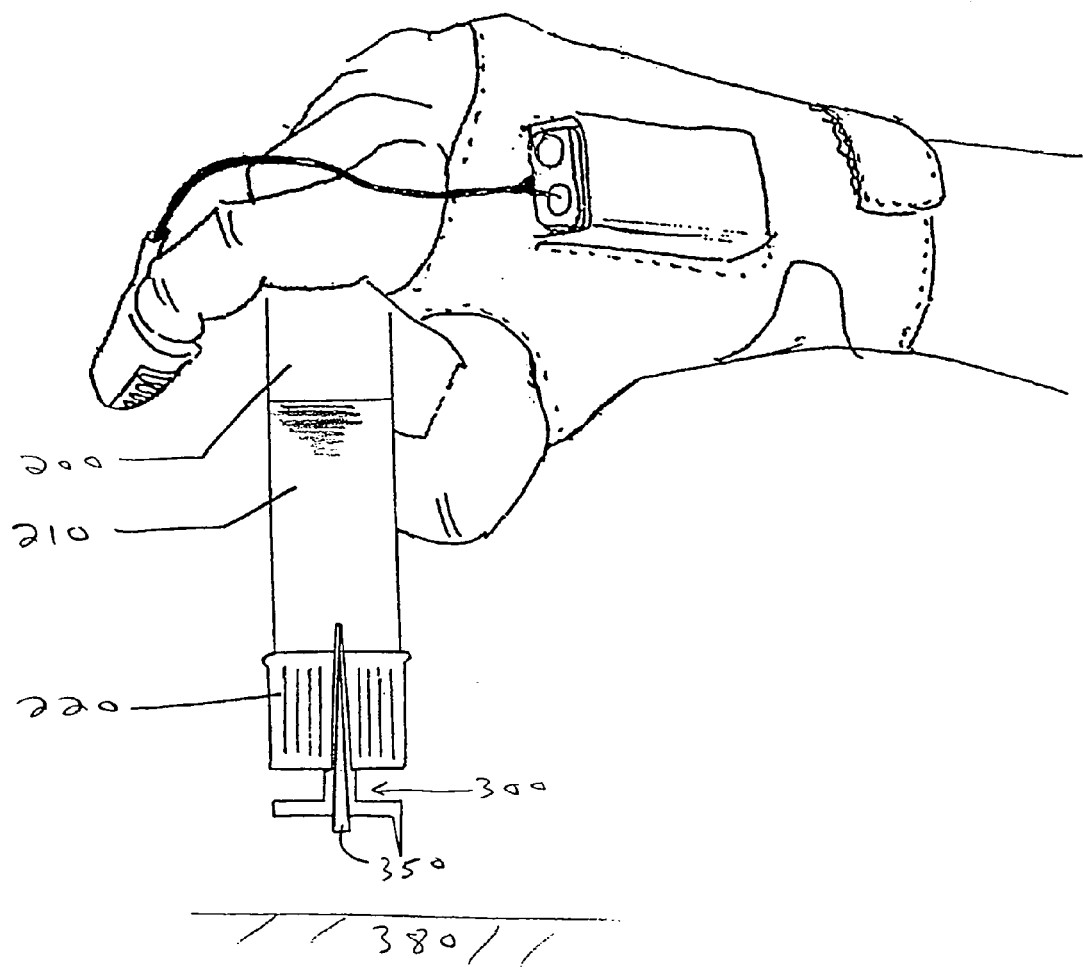

FIG. 9 shows the technician inverting the test tube 200. Because the test tube 200 is sealed, the pressure on the inside of the test tube 200 is equal to the pressure on the outside of the test tube 200. Therefore, no liquid is dispensed through channel 350.

At this point, methods using force would require the technician to generally apply a force or pressure to the system, causing a mechanical reaction and a consequent increase of pressure on the inside of the test tube 200. For example, a technician might apply a force to the dispensing apparatus 300, causing the rubber stopper 220 to flex inwardly. This inward flex would compress the contents of the test tube 200, resulting in a pressure increase on the interior of the test tube 200. The pressure differential between the interior and exterior of the test tube causes liquid to flow through channel 350 and dispense on surface 380.

Figure 10:
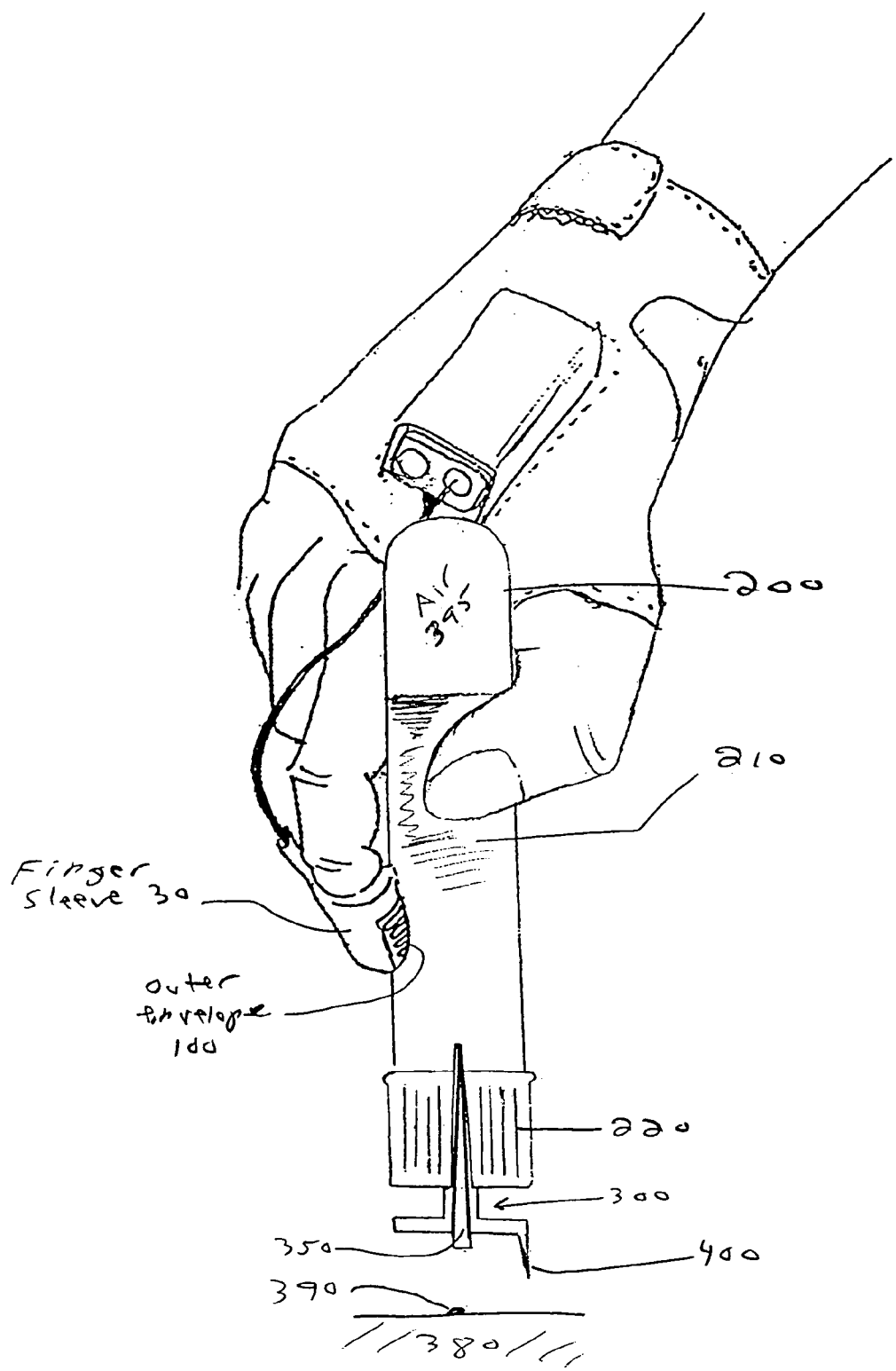

FIG. 10 shows how the present invention does away with the application of force or pressure. As shown in FIG. 10, the outer envelope 100 of the finger sleeve 30 is contacted on the outer surface of the test tube 200. Heat from heating surface 70 passes through the outer envelope 100 and is conducted onto the outer surface of the test tube 200. This heat is then transferred though the wall of the test tube 200 and conducted to the liquid 210 within the test tube 200.

The heated liquid 210 expands, causing an increase of pressure on the inside of test tube 200. The pressure on the outside of the test tube 200 has not changed, particularly the pressure at the end of channel 350. Thus, a pressure differential is created between the inside and outside of the test tube 200. This pressure differential forces liquid 210 to flow through channel 350 and deposit on surface 380 as a sample 390.

Although FIG. 10 shows heating the liquid 210, it may be preferable to heat air pocket 395. The expansion of heated air can cause the creation of a pressure differential as equally useful as the differential caused by expansion of the liquid. The heated air 395 forces liquid 210 through the channel 350 to deposit as a sample 390 on surface 380.

The deposited sample shown in FIG. 10 may be then be easily spread using the techniques previously discussed with respect to FIG. 4.

In the case where the liquid 210 is a hazardous, toxic, or infectious substance, the present method advantageously uses no physical force on the test tube stopper 220. Only a light touching of outer envelope 100 onto the wall of test tube 200 is required.

The technician does not press on the stopper 220, and risk shattering the test tube or causing a leak if excess pressure is used. The technician's hand is kept away from channel 350 at all times during depositing and distributing of the sample, reducing a chance exposure to the harmful substance 210. The entire operation may be performed with one hand, freeing the other hand to provide balance or adjust surface 380. Other advantages of the present invention, not discussed herein, are evident from the previous disclosure to one of ordinary skill in the art.

The method to dispose a sample of a liquid, described previously with respect to FIGS. 7, 8, 9, and 10, may be taken one step further. In a preferred embodiment, the heating apparatus 5 of the present invention is not required to deposit a sample, and no mechanical force need be used.

Figure 11:
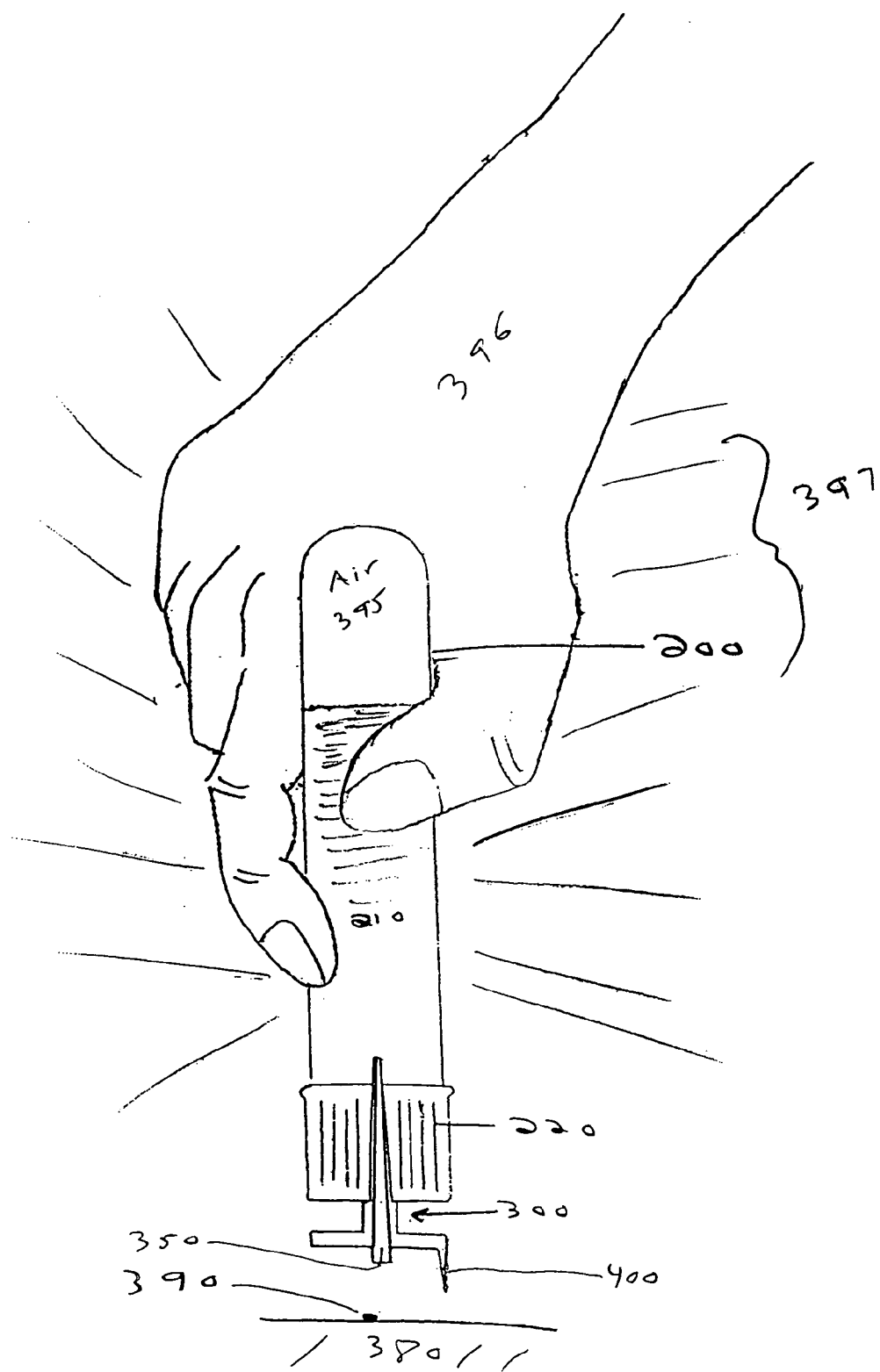
FIG. 11 is a diagrammatic illustration of the method and apparatus of an alternative embodiment of safely dispensing an distributing a hazardous substance from a storage container, where a technician's hand is used to apply heat to the storage container.

FIG. 11 shows a preferred embodiment similar to that of FIGS. 7, 8, 9, and 10, but without the heating apparatus 5 of the present invention. Prior to the orientation of the test tube 200 shown in FIG. 11, the steps previously shown with respect to FIGS. 7, 8, and 9 are performed, but without use of the heating apparatus 5. The orientation of the test tube 200 shown in FIG. 5 corresponds to that of FIG. 10, but does not use the heating apparatus 5.

As shown in FIG. 11, the technician simply grasps the test tube 200 with dispensing apparatus 300 using his or her hand 396. The natural body heat 397 from the technician's hand warms up the contents of the test tube 200, particularly the air pocket 295 and liquid 210. The resulting pressure differential forces liquid through channel 350. As a result, a sample 290 is disposed onto surface 380.

When using a hazardous liquid, it is advantageous that the technician wears a protective glove (not shown). The glove should be thermally conductive to carry heat from the technician's hand to the test tube 200.

As with the deposited sample shown and described with respect to FIG. 4, the technician may simply tilt the test tube 200 and spread the sample using paddle 400.

Although a technician has been discussed with respect to the previous disclosure of the invention, the simple steps performed by the technician (as described herein) may be performed by an automated or mechanized device, as will be appreciated by one of ordinary skill in the art.

In the embodiment of FIG. 11, which does not use the heating apparatus 5, it may be desirable to increase the temperature differential using additional methods. For example, the test tube 200 and its contents 210 may be cooled or refrigerated in advance. The resulting temperature differential when the refrigerated test tube 200 (containing refrigerated liquid 210) is grasped by a technician will be higher than if the test tube 200 and liquid 210 were at room temperature. The refrigeration method may also be used to increase the effectiveness of dispensing a liquid sample when using the heating apparatus 5, as described with respect to FIGS. 7, 8, 9, and 10.

The foregoing description of the present invention has been presented for purposes of illustration and description. Furthermore, the description is not intended to limit the invention to the examples described. Consequently, variations and modifications commensurate with the above teachings, and within the skill and knowledge of the relevant art, are considered to be part of the scope of the present invention. The embodiments described hereinabove are further intended to explain best modes known of practicing the invention and to enable others skilled in the art to utilize the invention in other embodiments and with various modifications required by the particular applications or uses of the present invention. It is intended that the appended claims be construed to include alternative embodiments to the extent permitted by the scope of the prior art.

What is claimed is:

1. An apparatus for dispensing a liquid sample from a test tube onto a surface and for distributing the sample on the surface, the apparatus comprising:
   a dispensing apparatus for dispensing a liquid sample from the test tube to the surface in response to a stimulus having an end through which the liquid dispenses; and
   a paddle connected at said end for distributing the dispensed sample on the surface, wherein said paddle is round.

2. The apparatus of claim 1, wherein the stimulus is mechanical pressure.

3. The apparatus according to claim 1, wherein the stimulus is an applied force and the test tube has a flexible cover, and wherein the dispensing apparatus comprises:
   a ledge for receiving the applied force;
   a shoulder, in contact with the flexible cover and connected to the ledge, for increasing the pressure on the inside of the test tube in response to the applied force on the ledge; and
   whereby a sample is dispensed from the test tube due to the increase of pressure on the inside of the tube.

4. The apparatus of claim 3, wherein said paddle receives said applied force.

5. The apparatus according to claim 3, wherein said ledge extends radially from the dispensing apparatus and has one end which connects the dispensing apparatus with the paddle.

6. The apparatus according to claim 1, wherein the test tube has a flexible cover and wherein the dispensing apparatus comprises:
   a tip for piercing the flexible cover to fasten the dispensing means to the test tube cover.

7. The apparatus according to claim 1, further comprising:
   a flexible test tube cover, connected to the test tube and in contact with the dispensing apparatus.

8. The apparatus according to claim 7, wherein the test tube cover is a rubber stopper, and wherein the dispensing apparatus comprises a tip for piercing the rubber stopper.

9. An apparatus for dispensing a liquid from a container onto a surface and distributing the dispensed sample on the surface, the apparatus comprising:
   first and second ends, the first end connected to the second end by a channel which carries liquid from the first end to the second end;
   an entrance and a pointed tip at the first end;
   an exit at the second end which dispenses a sample;
   a paddle, attached to the second end, and adapted to distribute the dispensed sample on the surface, wherein said paddle extends beyond said exit;
   a ledge that is perpendicular to the channel, wherein the paddle is attached to the second end by said ledge and wherein the paddle is substantially perpendicular to said ledge and tapers in a direction away from said ledge; and
   a shoulder, located between the first and second end, and having a diameter larger than the first end.

10. The apparatus according to claim 9, wherein said paddle is rectangular.

11. The apparatus according to claim 9, wherein said first end is tapered from said shoulder to said tip.

12. The apparatus according to claim 9, wherein said paddle is round.

13. The apparatus according to claim 9, wherein said channel is tapered from said shoulder to said entrance.

14. The apparatus according to claim 9, wherein said entrance is tapered toward said tip.

* * * * *